United States Patent [19]

Blount

[11] 4,094,825

[45] * June 13, 1978

[54] PROCESS FOR THE PRODUCTION OF PHENOL SILICOFORMATE COMPOUNDS AND THEIR CONDENSATION PRODUCTS

[76] Inventor: David H. Blount, 5450 Lea St., San Diego, Calif. 92105

[*] Notice: The portion of the term of this patent subsequent to Jun. 28, 1994, has been disclaimed.

[21] Appl. No.: 747,873

[22] Filed: Dec. 6, 1976

Related U.S. Application Data

[63] Continuation-in-part of Ser. No. 672,559, Mar. 31, 1976, Pat. No. 4,032,511, which is a continuation-in-part of Ser. No. 555,078, Mar. 3, 1975, abandoned.

[51] Int. Cl.² .............................................. C08G 2/00
[52] U.S. Cl. .................................. 260/2 S; 260/18 S; 260/46.5 R; 260/53 R; 260/448.8 R; 423/324; 423/325; 423/326
[58] Field of Search .............. 260/448.8 R, 2 S, 53 R, 260/18 S, 46.5 R; 423/324, 325, 326

[56] References Cited

U.S. PATENT DOCUMENTS 4,032,511  6/1977  Blount ........................... 260/46.5 R Primary Examiner—Melvyn I. Marquis

[57] ABSTRACT

Phenol compounds and silicoformic acid will chemically react to produce a phenol silicoformate when heated with a suitable alkali catalyst. The phenol silicoformate compounds are then chemically reacted with an aldehyde to form a condensation product.

15 Claims, No Drawings

PROCESS FOR THE PRODUCTION OF PHENOL SILICOFORMATE COMPOUNDS AND THEIR CONDENSATION PRODUCTS

CROSS-REFERENCE TO RELATED CO-PENDING APPLICATION

This application is a continuation-in-part of U.S. patent application Ser. No. 672,559, filed Mar. 31, 1976 now Pat. No. 4,032,511, which in turn is a continuation-in-part of U.S. patent application, Ser. No. 555,078, filed Mar. 3, 1975, now abandoned.

BACKGROUND OF THE INVENTION

This invention relates to a process for the production of phenol silicoformate resinous compounds by chemically reacting a silicoformic acid with a phenol compound while heating the mixture in the presence of an alkali catalyst, thereby producing a phenol silicoformate compound which is then heated with an aldehyde, thereby producing an aldehyde phenol silicoformate resinous compound.

The silicoformic acid used in this process may be produced by the chemical reaction of a dry alkaline earth metal metasilicate or a dry alkali metal metasilicate with a mineral acid or a hydrogen salt, as disclosed in my U.S. Pat. Nos. 3,956,466 and 3,962,111 and by other methods such as those disclosed in U.S. Pat. Nos. 3,674,430 and 3,937,782.

The silicoformic acid used in this process was analyzed by several methods. On chemical analysis of the washed and air dried silicoformic acid using hydroflouric acid, it contained 90% silicon dioxide, 5% water and 5% salt. The molecular weight studies were done by adding silicoformic acid to a sodium hydroxide aqueous solution and calculating the elevation in boiling point. This method gave a molecular weight of 78 ± 25 gm/mol which indicates that it is of a small molecular weight and not a polymeric form of silicate. This type of reactive solution normally changes the molecular species and probably changes the silicoformic acid to orthosilicoformic acid ($H_4SiO_3$). When orthosilicoformic acid loses $H_2O$ by dehydration, silicoformic acid is formed. The silicoformic acid was analyzed by Infrared Analysis and was found to be similar in nature to the Mallinckrodt's hydrated silica, $SiO_2 \cdot xH_2O$, except for the presence of Si-H bonds which gave a definite absorption peak at 615 $cm^{-1}$. There may also be a small amount of hydrated silica present. Further evidence of the Si—H bonds are shown by the ability of the said compound to reduce an aqueous solution of silver nitrate. The silicoformic acid has the chemical properties of a weak acid and readily reacts chemically with alkali metal hydroxides and is readily soluble in dilute alkali metal hydroxide aqueous solutions.

Phenol silicoformate compounds will chemically react with diisocyanates, dicarboxyl acids and anhydrides, ketones, furans and aldehydes to produce useful resinous compounds which may be dissolved in organic solvents such as acetic acid and may be used as a coating agent to protect wood. Phenol silicoformates may be used as fillers in paints and varnishes. The aldehyde phenol silicoformates may be used as molding powders then heated to the softening point and molded into useful objects such as tool handles, ash trays, etc. The alkdehyde phenol silicoformate resins may be used as casting resins by pouring the said liquid resin into a mold and continuing to heat until an insoluble solid resin is formed, thereby producing useful objects. Solutions of aldehyde phenol silicoformate resins may be used as adhesives, paints, varnishes, impregnants and laminates.

SUMMARY OF THE INVENTION

I have discovered that silicoformic acid and silica hydrate will react chemically with phenols in the presence of a small amount of alkali catalyst at a temperature just below the boiling temperature of the phenol to produce a phenol silicoformate when a 1:1 mol ratio is used. When two mols of silicoformic acid are reacted with one mol of resorcinol, a resorcinol disilicoformate is produced.

While all of the details of the reactions which take place are not fully understood, it appears that the silicoformic acid generally reacts with one of the hydroxyl groups of the phenol compound to produce a phenol silicoformate compound. The chemical reaction is theorized to take place as follows:

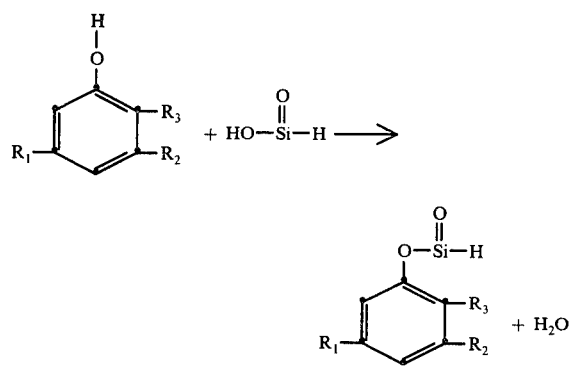

wherein $R_1$, $R_2$ and $R_3$ are selected from the group consisting of hydrogen, hydroxyl radicals, carboxyl radicals, hydrocarbon radicals, alkali radicals, aryl radicals, and benzyl radicals.

The phenol silicoformate compound will further react with organic aldehydes to produce poly(aldehyde phenol silicoformate) resins.

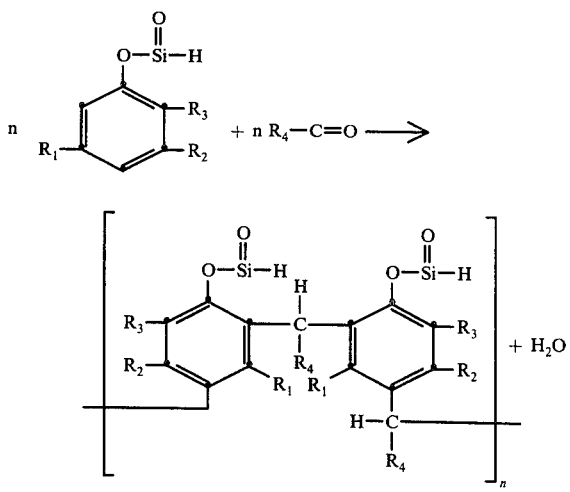

wherein $n$ is a positive integer greater than one; wherein $R_1$, $R_2$, and $R_3$ are chosen from the group consisting of hydrogen, hydroxyl radicals, carboxyl radicals and hydrocarbon radicals. Wherein $R_4$ is chosen from the group consisting of hydrogen, hydrocarbon radicals, and amine radicals. The silica hydrate will react with the phenols similar to the way silicoformic acid does.

DETAILED DESCRIPTION OF THE INVENTION

Any suitable phenol compound may be used in my novel process. Typical phenols include phenol, m-cresol, P-cresol, o-cresol, xylenols, resorcinol, cashew nut shell liquids, anacordol, P-tert-butyl phenol, P-tert-amyl phenol, p-phenyl phenol, anacardic acid, Bis-phenol A, creosote oil, chlorophenol, nitrophenol hydroquinone, pyrogallol and naphthol.

Any suitable alkali catalyst may be used to promote the reaction. The catalytic mechanism which takes place is not fully understood. The alkali may act as a catalyst directly, or it may react slightly with one or the other of the primary reactants. From about 1 to 10 weight percent catalyst (based on the weight of the reactants, silicoformic acid and phenol compound used) gives the best results. Since the alkali can react with the silicoformic acid and phenol compound, the use of large amounts of alkali should be avoided. Typical alkali includes alkali metal carbonates, hydroxides, oxides and salts of weak acids. The preferred catalysts are the alkali metal carbonates, with best results being obtained with sodium carbonate.

The phenol silicoformate compounds produced by this method are cream to reddish brown in color, granular, and soften when heated to about 80° C but are destroyed by further heating. The phenol silicoformate compounds are soluble in aqueous formaldehyde, aldehydes, polyalcohols, acetic acid, acetone, dilute alkali metal solutions, dilute sulfuric acid and other organic solvents.

Various aldehydes may be used to produce poly(aldehyde phenol silicoformate) resins such as formaldehyde, acetaldehyde, butylaldehyde, chloral, acrolein, paraformaldehyde, and furfural. The aldehyde ratio may vary from about 0.5 to 3 mols of aldehyde to one mol of phenol silicoformate, depending on the methyol groups desired.

Various catalysts may be used to enhance the reaction between phenol silicoformate compounds and aldehydes. They may be acidic, basic or neutral. Some of the acid catalysts which may be used are sulfuric acid, sodium hydrogen sulfate, hydrochloric acid, formic acid, acetic acid, oxalic acid, tartaric acid and aromatic sulfonic acid. Some of the basic catalysts are sodium carbonate, sodium silicate, ammonia, sodium hydroxide, potassium hydroxide, calcium hydroxide, urea and quatarnary ammonium hydroxide.

The preferred method of this invention is to produce a formaldehyde phenol silicoformate resinous product by heating phenol and silicoformic acid in the ratio of 1:1 mols in the presence of an alkali catalyst, sodium carbonate, thereby producing a tan, granular phenol silicoformate. An aqueous formaldehyde solution is added in the ratio of 1 to 3 mols to each mol of phenol silicoformate and is heated until an aldehyde phenol silicoformate product is produced. In an alternative embodiment, an acid catalyst is added to the mixture of phenol silicoformate and formaldehyde until the pH is 4 to 6, then heated until a formaldehyde phenol silicoformate resinous product is produced.

DESCRIPTION OF PREFERRED EMBODIMENTS

The following examples which describe certain preferred embodiments of the processes may, of course, be varied as described above with similar results. Parts and percentages are by weight unless otherwise indicated.

EXAMPLE I

Dry granular sodium metasilicate pentahydrate is slowly added to concentrated sulfuric acid in the ratio of 1:1 mols and mixed; $O_2$ is evolved and considerable heat is created. The reaction is complete in 2 to 6 hours, thereby producing a white granular mixture of silicoformic acid and sodium sulfate. The silicoformic acid is washed with water to remove the sodium sulfate, then air dried at 25° to 75° C.

The silicoformic acid is then mixed with phenol in the ratio of 1:1 mols, then sodium carbonate in the ratio of 2 parts by weight per 100 parts of silicoformic acid and phenol, are added to catalyze the reaction. The mixture is then agitated and heated to 50° to 75° C for 20 to 40 minutes until the chemical reaction is complete and phenol silicoformate is produced (a tan granular compound).

An aqueous solution of formaldehyde is added to the phenol silicoformate in the ratio of 1 to 1 mols, and the mixture is heated to 65° to 85° C while agitating for 10 to 90 minutes or until the desired viscosity is obtained; if heating continues, a solid mass will be formed, thereby producing a reddish colored formaldehyde phenol silicoformate resinous product.

Chemical reactions to produce formaldehyde phenol silicoformate resinous compound are believed to occur as follows:

$$2Na_2SiO_3 + 2H_2SO_4 \rightarrow 2H\cdot SiO\cdot OH + O_2 + 2Na_2SO_4 \quad (1)$$

$$H_6C_5OH + H\cdot SiO\cdot OH \rightarrow H_6C_5OSiOH + H_2O \quad (2)$$

$$H_6C_5OSiOH + H_2CO \rightarrow resin \quad (3)$$

EXAMPLE II

Dry granular sodium metasilicate is gradually added to concentrated sulfuric acid in the ratio of 1:2 mols while agitating and keeping the temperature between 50° to 85° C. The reaction is complete in 2 to 6 hours, thereby producing silicoformic acid and sodium hydrogen sulfate. The mixture is washed and filtered to remove the salt from the silicoformic acid.

Cresol is mixed with the silicoformic acid in the ratio of about 1:1 mols. Sodium carbonate is added to the mixture in the ratio of 5 parts by weight per 100 parts of combined weight of cresol and silicoformic acid. The mixture is then heated to 50° to 80° C while agitating for 20 to 45 minutes, thereby producing brown granules of cresol silicoformate.

An aqueous solution of 37% formaldehyde is added to the cresol silicoformate in the ratio of about 1 to 1 mols. Dilute sulfuric acid is added until a pH of about 7 is reached, and the cresol silicoformate goes into solution. The solution is heated to 50° to 75° C for 10 to 45 minutes until a light brown, resinous compound of the desired viscosity is formed. The resin separates from the water and is removed. The formaldehyde cresol silicoformate resinous compound is soluble in acetone and other organic solvents.

EXAMPLE III

Dry granular potassium metasilicate is mixed with potassium hydrogen sulfate in the ratio of 1 to 2 mols; the mixture produces considerable heat, and oxygen is evolved in 1 to 6 minutes; the reaction is complete in about 1 hour, thereby producing white granular silicoformic acid and potassium sulfate. The mixture is then washed and filtered to remove the salt.

The silicoformic acid is mixed with resorcinol in the ratio of about 1 to 1 mols; then potassium carbonate is added in the ratio of 1 part by weight for each 10 parts of combined weight of silicoformic acid and resorcinol. The mixture is then heated to 50° to 85° C for 20 to 45 minutes while agitating, thereby producing light brown granules of resorcinol silicoformate.

Formaldehyde in aqueous solution is added to the granules of resorcinol silicoformate acid in the ratio of about 1 to 1 mols. Sodium hydroxide is added until the pH is between 10 to 12. The mixture is then heated to 50° to 85° C while agitating and the resorcinol silicoformate goes into solution. In 30 to 90 minutes the reaction is complete, thereby producing a formaldehyde resorcinol silicoformate resinous compound. This compound is soluble in acetone and other organic solvents.

An acetone solution of the resinous product may be painted on wood and forms a tough protective coating.

EXAMPLE IV

Silicoformic acid and phenol are mixed in a 1 to 1 mol ratio; then one part by weight of sodium carbonate is added per 100 parts of combined weight of silicoformic acid and phenol. The mixture is then heated to 50° to 85° C for 20 to 45 minutes, thereby producing tan granules of phenol silicoformate. The phenol silicoformate is soluble in aqueous aldehyde solutions, acetone, glycerol, dilute alkali metal solutions, dilute sulfuric acid solutions, acetic acid and other organic solvents.

The phenol silicoformate may be added to varnishes and paints and used as a filler.

EXAMPLE V

The tan granules of phenol silicoformate as produced in Example VI are mixed in an aqueous solution containing 37% formaldehyde in the ratio of 1 to 3 mols then heated at 65° to 100° C for 10 to 90 minutes while agitating until the desired viscosity is obtained, thereby producing a reddish resinous compound. The resinous compound may be produced in a thick liquid form, in a soft solid resin, or if heating continues, the resin will form a hard, insoluble resin. A reflux condenser and a vacuum may be used to remove the water.

The liquid resinous product produced may be poured into molds to make useful objects, then heated until a hard, tough useful object is produced.

EXAMPLE VI

The tan granules of phenol silicoformate as produced in Example IV are mixed with an aqueous solution containing about 37% formaldehyde, in the ratio of 1 to 2 mols, then dilute hydrochloric acid is added until the pH is about 4 to 5. The mixture is heated to 80° to 100° C while agitating and the phenol silicoformate goes into solution. The solution is then filtered, and about 10 to 15% of the silicoformic acid is filtered out. The mixture is then heated to 80° to 100° C while agitating for 20 to 90 minutes or until the desired viscosity is obtained. The cream colored, resinous compound may be produced in the form of a thick liquid or a solid resin.

The said resinous compound is soluble in acetic acid, glycerol, vegetable oils, acetone, polyalcohols and other organic solvents. A solution of the said resin may be used as an adhesive to glue wood together and may be used in paints, varnishes and laminates.

The said resin may be used as a molding powder by mixing with hexamethylene tetramine, placing the mixture in a mold, then applying heat at 85° to 110° C followed by pressure, thereby producing useful objects which are solid and tough.

EXAMPLE VII

Dry granular silicoformic acid and phenol are mixed in the ratio of about equal mols, then sodium hydroxide is added in the ratio of 1 part by weight to about 100 parts by weight of silicoformic acid and phenol. The mixture is then heated to just below the boiling point of phenol while agitating for 20 to 80 minutes, thereby producing tan granules of phenol silicoformate.

About 1 mol of phenol silicoformate and one mol of furfural are mixed then heated to just below the boiling point of furfural for 10 to 60 minutes until the desired viscosity is obtained, thereby producing a brown resinous product. The said resin may be produced as a thick, brown liquid, a brown fusable solid or an infusable solid, depending on the length of time that the resin is heated.

The furfural phenol silicoformate resinous product is soluble in acetic acid, acetone, polyalcohols, oils and other organic solvents. A solution of the said resinous product may be used as a protective coating on wood. The thick, brown, liquid, resinous product may be cured to produce a hard tough solid resin by the addition of a mineral acid until the pH is 4 to 5.

EXAMPLE VIII

Dry granular silicoformic acid and phenol are mixed in the ratio of about equal mols; then sodium carbonate is added in the ratio of 1 part by weight to 20 parts of combined weight of silicoformic acid and phenol. The mixture is then heated to just below the boiling point of phenol while agitating for 20 to 80 minutes, thereby producing tan granules of phenol silicoformate.

The phenol silicoformate compound and crotonaldehyde are mixed in about an equal molar ratio then heated to 70° to 90° C while agitating for 20 to 70 minutes, thereby producing a yellow, resinous product, crotonaldehyde phenol silicoformate. The resin is soluble in acetic acid.

EXAMPLE IX

The tan granules of phenol silicate as produced in Example VIII and acrolein are mixed in a ratio of about 1 to 1 mols. The mixture is then heated to just below the boiling point of acrolein while agitating for 20 to 80 minutes, thereby producing a resinous product.

EXAMPLE X

Tan granules of phenol silicate as produced in Example VIII are added to about equal mols of furfural, then dilute sulfuric acid is added to the mixture until the pH is about 4 to 5 while agitating for 10 to 20 minutes, thereby producing a brown, resinous product.

EXAMPLE XI

Dry granular silicoformic acid and equal parts by weight of creosote oil are mixed with 10% by weight of dry sodium metasilicate granules, calculated on the combined weight of silicoformic acid and creosote oil; the mixture is then heated to 100° to 160° C while agitating for 10 to 60 minutes, thereby producing brown granules of creosote silicoformate.

The creosote silicate is added to an aqueous solution containing about 37% formaldehyde in the ratio of 1 to 2 parts by weight. The mixture is then heated to 80° to 120° C while agitating for 20 to 80 minutes, thereby producing a brown, resinous product.

EXAMPLE XII

Dry granular silicoformic acid and cresylic acid are mixed in the ratio of 1 to 2 parts by weight, then about 5% by weight of sodium carbonate is added. The mixture is then heated to just below the boiling point of cresylic acid for 20 to 60 minutes while agitating, thereby producing brown granules of phenol silicoformate and cresol silicoformate.

The phenol silicoformate and cresol silicoformate are added to an aqueous solution containing 37% formaldehyde in the ratio of about equal parts by weight. The mixture is then heated to 80° to 120° C while agitating for 20 to 80 minutes, thereby producing a brown, resinous product.

EXAMPLE XIII

Cresylic acid and silicoformic acid are mixed in about equal molar proportions; the mols of cresylic acid are based on the cresol and phenol content of the cresylic acid; then an amount of sodium carbonate is added equal to 10% by weight of the cresylic acid and silicoformic acid. The mixture is then heated to just below the boiling point of cresylic acid while agitating for 15 to 45 minutes, thereby producing a brown granular mixture of phenol silicoformate and cresol silicoformate.

EXAMPLE XIV 2 mols of cresol, about 1 mol of granular silicoformic acid and 5% by weight of sodium carbonate, based on the weight of silicoformic acid and cresol, are mixed then heated to just below the boiling point of cresol at ambient pressure while agitating for about 30 minutes, thereby producing light brown granules of cresol silicoformate.

Cresol silicoformate and an aqueous solution containing 37% formaldehyde are mixed in the ratio of 1 to 2 mols; then acetic acid is added until the pH is 4 to 6. The mixture is then heated to 80° to 120° C for 20 to 80 minutes or until the desired viscosity is obtained, thereby producing a cream colored, resinous product.

The cream colored, resinous product is soluble in acetone; it may be painted on wood and forms a tough protective coating.

EXAMPLE XV

One part by weight of dry granular silicoformic acid, 2 parts by weight of creosote, 5% potassium hydroxide by weight, based on the weight of silicoformic acid and creosote, are mixed then heated to 80° to 120° C while agitating for 20 to 60 minutes at ambient pressure, thereby producing brown granules of creosote silicoformate.

About equal parts by weight of creosote silicoformate and furfuryl alcohol are mixed; then dilute hydrochloric acid is added until the pH is between 4 to 6 while agitating for 10 to 20 minutes, thereby producing a brown, resinous product.

The brown, resinous product is soluble in acetone; it may be painted on wood and forms a tough protective coating.

Although certain specific preferred ingredients and conditions are described in conjunction with the above detailed description of the Invention and Examples, these may be varied and other ingredients may be used where suitable, with similar results. For example, various cross-linking or modifying agents may be used.

Other applications, modifications and ramifications of this invention will occur to those skilled in the art upon reading this disclosure. These are intended to be included within the scope of this invention, as defined in the appended claims.

I claim:

1. The process for the production of phenol silicoformate compounds by the following steps:
   (a) mixing silicoformic acid and a phenol compound,
   (b) adding an alkali catalyst equal to 1 to 10% by weight of silicoformic acid and phenol compound,
   (c) heating said mixture to just below the boiling point of the phenol compound for 20 to 80 minutes while agitating at ambient pressure, thereby
   (d) producing a granular phenol silicate compound.

2. The method of claim 1 wherein the phenol compound is selected from the group consisting of phenol, p-cresol, o-cresol, m-cresol, cresylic acid, xylenols, resorcinol, cashew nut shell liquids, anacordol, p-tert-butyl pheol, anacardic acid, Bisphenol A, creosote oil, 2,6-dimethylphenol, and mixtures thereof.

3. The method of claim 1 wherein the alkali catalyst is an alkali metal carbonate, selected from the group consisting of sodium carbonate and potassium carbonate.

4. The method of claim 1 wherein the alkali catalyst is as alkali metal hydroxide, selected from the group consisting of sodium hydroxide and potassium hydroxide.

5. The method of claim 1, including the further steps, following step (d), of:
   (a) adding an aldehyde in the ratio of 1 to 3 mols to each mol of the phenol compound,
   (b) heating said mixture at 50° to 120° C for 20 to 90 minutes while agitating, thereby
   (c) producing a resinous product.

6. The method of claim 5 wherein the aldehyde is selected from the group consisting of formaldehyde, acetaldehyde, butylaldehyde, chloral, acrolein, paraformaldehyde, furfural and mixtures thereof.

7. The method of claim 5 including the further step of adding an acid catalyst until the pH is 3 to 6 following step (a) and before step (b) of Claim 5.

8. The method of claim 7 wherein the acid catalyst is selected from the group consisting of sulfuric acid, hydrochloric acid, acetic acid, formic acid, oxalic acid, tartaric acid, aromatic sulfonic acid, sodium hydrogen sulfate and mixtures thereof.

9. The method of claim 1 wherein the phenol compound is phenol.

10. The method of claim 5 wherein the aldehyde is formaldehyde in an aqueous solution.

11. The method of claim 7 wherein the acid catalyst is added until the pH is about 7.

12. The product, phenol silicate compounds, produced by the method of claim 1.

13. The product, resinous products, produced by the method of claim 5.

14. The method of claim 1 wherein the silicoformic acid is produced by the following steps:
(a) adding about one mol of dry granular alkali metal metasilicate slowly to 1 to 2 mols of concentrated sulfuric acid;
(b) agitating said mixture to keep the temperature below 100° C and oxygen evolves from the mixture, thereby
(c) producing a white granular mixture of alkali metal sulfate and silicon acid compounds consisting of silicoformic acid and hydrated silica;
(d) washing said mixture with water, filtering the mixture to remove the alkali sulfate and then air drying at 25° to 75° C, leaving a fine white granular mixture of silicoformic acid and hydrated silica.

15. The method of claim 1 wherein the silicoformic acid is mixed with the phenol compound in the ratio of 1:1 to 1:2 mols; the mols of silicoformic acid are calculated on the basis of the silicon dioxide content.

* * * * *